US011896503B2

(12) United States Patent
Farina et al.

(10) Patent No.: US 11,896,503 B2
(45) Date of Patent: Feb. 13, 2024

(54) METHODS FOR ENABLING MOVEMENT OF OBJECTS, AND ASSOCIATED APPARATUS

(71) Applicant: IMPERIAL COLLEGE INNOVATIONS LIMITED, London (GB)

(72) Inventors: Dario Farina, London (GB); Benjamin Lakey, London (GB); Ivan Vujaklija, London (GB); Irene Mendez, London (GB)

(73) Assignee: IMPERIAL COLLEGE INNOVATIONS LIMITED, London (GB)

(*) Notice: Subject to any disclaimer, the term of this patent is extended or adjusted under 35 U.S.C. 154(b) by 401 days.

(21) Appl. No.: 17/260,924

(22) PCT Filed: Jul. 16, 2019

(86) PCT No.: PCT/GB2019/051982
§ 371 (c)(1),
(2) Date: Jan. 15, 2021

(87) PCT Pub. No.: WO2020/016567
PCT Pub. Date: Jan. 23, 2020

(65) Prior Publication Data
US 2021/0259859 A1    Aug. 26, 2021

(30) Foreign Application Priority Data

Jul. 16, 2018  (GB) ...................... 1811641

(51) Int. Cl.
*A61F 2/72*   (2006.01)
*A61B 5/389*  (2021.01)
(Continued)

(52) U.S. Cl.
CPC ................ *A61F 2/72* (2013.01); *A61B 5/389* (2021.01); *A61B 5/4851* (2013.01);
(Continued)

(58) Field of Classification Search
CPC ...... A61F 2/72; A61F 2/54; A61F 2/70; A61F 2002/704; A61B 5/389; A61B 5/4851; A61B 5/6811
See application file for complete search history.

(56) References Cited

U.S. PATENT DOCUMENTS 777,331 A    12/1904   Carrigan
787,074 A    4/1905    Buehne
(Continued)

FOREIGN PATENT DOCUMENTS

CN    106923942    7/2017
WO    0165513      9/2001
(Continued)

OTHER PUBLICATIONS

Amsuess, et al., "Context-Dependent Upper Limb Prosthesis Control for Natural and Robust Use," IEEE Transactions on Neural Systems and Rehabilitation Engineering, 24(7): 744-753 (2016).
(Continued)

*Primary Examiner* — Bruce E Snow
(74) *Attorney, Agent, or Firm* — PABST PATENT GROUP LLP

(57) ABSTRACT

A method for enabling movement of an object, having a plurality of degrees of freedom, by a user. The method comprising: receiving a first and second plurality of reference signals from first and second test subjects respectively, generated in response to respective reference intended movements; and determining a set of first of and second profiles. The method also comprises determining profile-pairs, which each comprise a first profile and a second
(Continued)

profile that correspond to the same degree of freedom of the object; determining a reference set of profiles based on a mathematical combination of each profile-pair; and providing the reference set of profiles for determining an intended movement of the object based on a plurality of user signals received from a respective plurality of different sensors associated with the user. The intended movement comprises simultaneous movements with respect to at least two degrees of freedom of the plurality of degrees of freedom.

15 Claims, 8 Drawing Sheets

(51) Int. Cl.
*A61B 5/00* (2006.01)
*A61F 2/54* (2006.01)
*A61F 2/70* (2006.01)

(52) U.S. Cl.
CPC .............. *A61B 5/6811* (2013.01); *A61F 2/54* (2013.01); *A61F 2/70* (2013.01); *A61F 2002/704* (2013.01)

(56) References Cited

U.S. PATENT DOCUMENTS

| | | | |
|---|---|---|---|
| 9,294,802 | B1 | 3/2016 | Nichols |
| 9,600,030 | B2 | 3/2017 | Bailey |
| 9,788,789 | B2 | 10/2017 | Bailey |
| 9,807,221 | B2 | 10/2017 | Bailey |
| 9,880,632 | B2 | 1/2018 | Ataee |
| 2013/0046394 | A1 | 2/2013 | Lipschutz |
| 2013/0338540 | A1* | 12/2013 | Hargrove ............... A61B 5/11 600/595 |
| 2014/0018938 | A1 | 1/2014 | Bertels |
| 2014/0032462 | A1 | 1/2014 | Lock |
| 2014/0334083 | A1 | 11/2014 | Bailey |
| 2014/0364703 | A1 | 12/2014 | Kim |
| 2015/0025355 | A1 | 1/2015 | Bailey |
| 2015/0064662 | A1 | 3/2015 | Slutzky |
| 2015/0320575 | A1 | 11/2015 | Joshi |
| 2015/0327808 | A1 | 11/2015 | Vice |
| 2017/0025026 | A1 | 1/2017 | Ortiz Catalan |

FOREIGN PATENT DOCUMENTS

| | | | |
|---|---|---|---|
| WO | 2008022435 | 2/2008 | |
| WO | 2012161657 | 11/2012 | |
| WO | 2014197401 | 12/2014 | |
| WO | 2015094112 | 6/2015 | |
| WO | 2016022621 | 2/2016 | |
| WO | WO-2020016567 A1 * | 1/2020 | ............. A61B 5/316 |

OTHER PUBLICATIONS

Hahne, et al., "Concurrent adaptation of human and machine improves simultaneous and proportional myoelectric control", IEEE Transactions on Neural Systems and Rehabilitation Engineering, 23(4):618-27 (2015).
Hahne, et al., "Simultaneous control of multiple functions of bionic hand prostheses: Performance and robustness in end users", Sci Robot., 3(19):1-10 (2018).
Hahne, et al., "User adaptation in Myoelectric Man-Machine Interfaces", Sci. Rep., 7(4437):1-10 (2017).
International Search Report for corresponding PCT application PCT/GB2019/051982 dated Oct. 24, 2019.
Jiang, et al., "Intuitive, Online, Simultaneous, and Proportional Myoelectric Control Over Two Degrees-of-Freedom in Upper Limb Amputees", IEEE Transactions on Neural Systems and Rehabilitation Engineering, 22(3): 501-510 (2014a).
Jiang, et al., "EMG-based simultaneous and proportional estimation of wrist/hand kinematics in uni-lateral trans-radial amputees", J. NeuroEngineering Rehabil., 9(42):1-11 (2012).
Jiang, et al., "Is accurate mapping of EMG signals on kinematics needed for precise online myoelectric control?" IEEE Transactions on Neural Systems and Rehabilitation Engineering, 22(3):549-58 (2014b).
Muceli, et al., "Simultaneous and Proportional Estimation of Hand Kinematics From EMG During Mirrored Movements at Multiple Degrees-of-Freedom", IEEE Transactions on Neural Systems and Rehabilitation Engineering, 20(3): 371-378 (2012).
Search Report for GB1811641.8 dated Jan. 25, 2019.

* cited by examiner

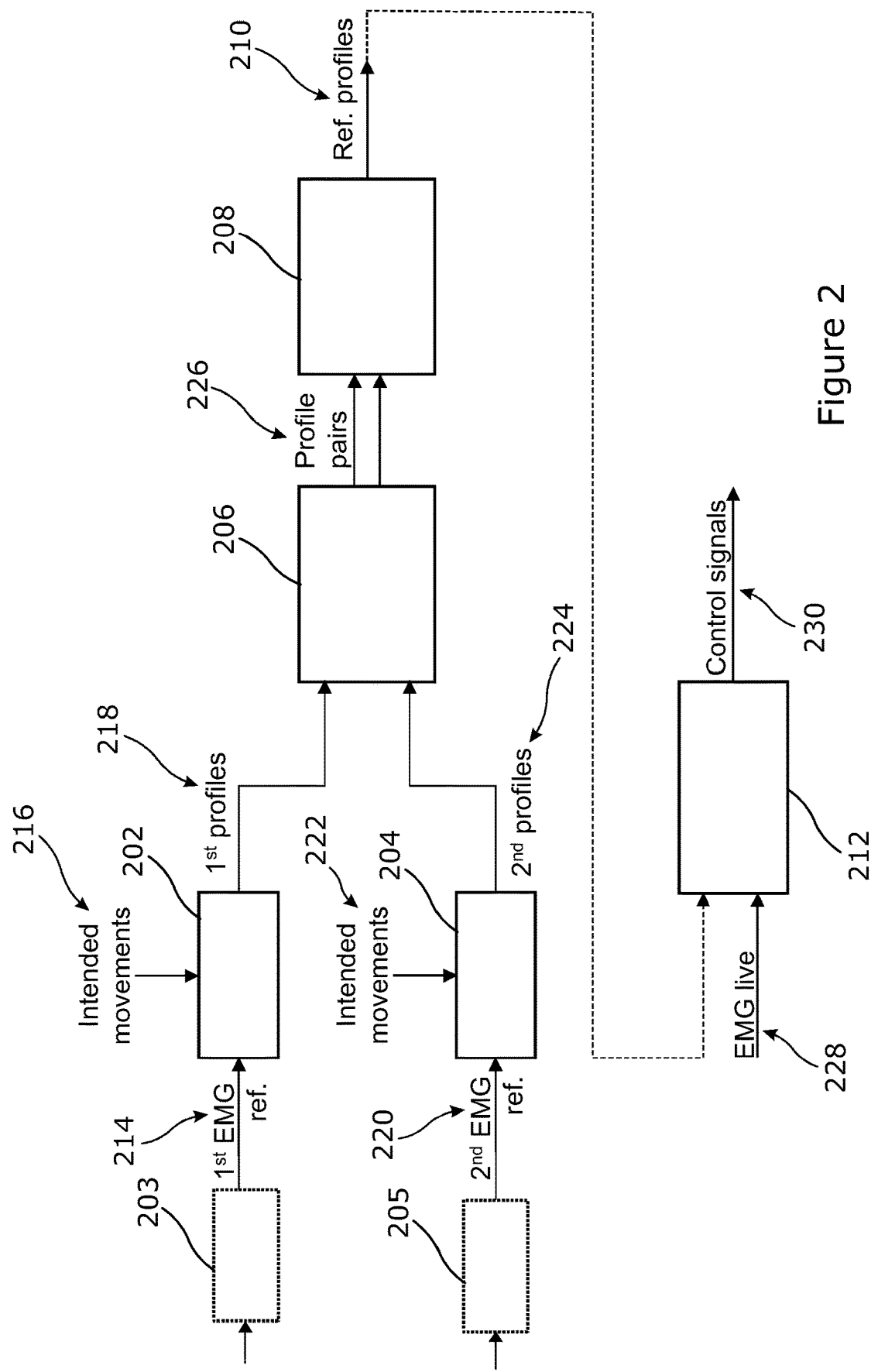

METHODS FOR ENABLING MOVEMENT OF OBJECTS, AND ASSOCIATED APPARATUS

CROSS-REFERENCE TO RELATED APPLICATIONS

This application is a National Phase application under 35 U.S.C. 371 of PCT/GB2019/051982, filed Jul. 16, 2019, and claims the benefit of and priority to G.B. Application No. 1811641.8, filed Jul. 16, 2018, the disclosures of which are hereby incorporated herein by reference in their entirety.

The present disclosure relates to methods for enabling movement of an object, and in particular, although not exclusively, to methods of processing EMG signals for controlling movement of prosthetic limbs.

According to a first aspect of the present disclosure there is provided a method for enabling movement of an object, having a plurality of degrees of freedom, by a user, the method comprising:

receiving a first plurality of reference signals from one or more sensors associated with a first test subject, the first plurality of signals generated in response to a plurality of reference intended movements (optionally the plurality of reference intended movements relate to each of the plurality of degrees of freedom of the object);

determining a set of first profiles based on the first plurality of reference signals and the plurality of reference intended movements;

receiving a second plurality of reference signals from one or more sensors associated with a second test subject, the second plurality of reference signals generated in response to a plurality of reference intended movements (optionally the plurality of reference intended movements relate to each of the plurality of degrees of freedom of the object);

determining a set of second profiles based on the second plurality of reference signals and the plurality of reference intended movements;

determining profile-pairs, wherein each profile-pair comprises a first profile and a second profile that correspond to the same degree of freedom of the object;

determining a reference set of profiles based on a mathematical combination of the first profile and the second profile of each profile-pair (optionally the reference set of profiles corresponds to each of the plurality of degrees of freedom); and providing the reference set of profiles for determining an intended movement of the object based on a plurality of user signals received from one or more sensors associated with the user, wherein the intended movement comprises simultaneous movements with respect to at least two degrees of freedom of the plurality of degrees of freedom.

Advantageously, such a method can provide the reference set of profiles such that it is suitable for use by other users, without requiring the other users to perform calibration operations on a per-person basis. Also advantageously, the method generates reference profiles that enable simultaneous and proportional control of the prosthetic limb with respect to at least two degrees of freedom using online data.

The first plurality of reference signals may comprise a first plurality of reference myography signals. The second plurality of reference signals may comprise a second plurality of reference myography signals. Providing the reference set of profiles for determining an intended movement of the object may be based on a plurality of user myography signals. The intended movement may comprise proportional and simultaneous movements.

The first plurality of reference signals may comprise a first plurality of reference myoelectric signals received from a respective plurality of different sensors associated with the first subject. The second plurality of reference signals may comprise a second plurality of reference myoelectric signals received from a respective plurality of different sensors associated with the second user. Providing the reference set of profiles for determining an intended movement of the object may be based on a plurality of user myoelectric signals received from a respective plurality of different sensors associated with the user. The sensors may comprise respective pluralities of electrodes, and/or they may be in contact with the user/subject.

The first set of profiles may comprise a first profile matrix. Determining the first profile matrix may comprise:

determining a first estimation matrix representative of samples of the first plurality of reference signals for the reference intended movements;

determining or receiving a first activation coefficient matrix, which is representative of a plurality of reference intended movements associated with the first plurality of reference signals; and determining a factorisation of the first estimation matrix into the first profile matrix and the first activation coefficient matrix.

Each coefficient of the estimation matrix may comprise a time domain representation of and/or spectral moment characteristics of the sample of the respective one of the plurality of user signals.

Each coefficient of the first estimation matrix may comprise a root mean square of a sample of a respective one of the first plurality of reference signals. A non-zero coefficient of the first activation coefficient matrix may correspond to a chosen kinetics or kinematics of a movement of the associated degree of freedom of the object which may include a chosen speed and/or force or torque.

Determining the first profile matrix may comprise performing a constrained optimisation computation configured to minimise (or reduce to an acceptably low level) the set difference cost function between (i) the first estimation matrix and (ii) a product of the first profile matrix and the first activation coefficient matrix. The constrained optimisation computation may be constrained to require a sparseness of the first profile matrix to be within a predetermined range.

Each second set of profiles may comprise a second profile matrix. Determining each second profile matrix may comprise:

determining a second estimation matrix representative of samples of the second plurality of reference signals for the reference intended movements;

determining or receiving a second activation coefficient matrix, which is representative of a plurality of reference intended movements associated with the second plurality of reference signals; and determining a factorisation of the second estimation matrix into the second profile matrix and the second activation coefficient matrix.

Each coefficient of the second estimation matrix may comprise a root mean square of a sample of a respective one of the second plurality of reference signals. A non-zero coefficient of the second activation coefficient matrix may correspond to a speed and/or a force or a torque of a movement of the associated degree of freedom of the object.

Determining the second set of profiles may comprise performing a constrained optimisation computation configured to minimise (or reduce to an acceptably low level) the set difference cost function between (i) the second estimation matrix and (ii) a product of the second profile matrix and the second activation coefficient matrix. The constrained optimisation computation may be constrained to require a sparseness of the second profile matrix to be within a predetermined range.

The plurality of degrees of freedom may include a first pair of opposing movements and a second different pair of opposing movements. The intended movement may comprise simultaneous movements of at least:
one of the first pair of opposing movements; and
one of the second different pair of opposing movements.

At least one of the plurality of degrees of freedom of the object may correspond to a pair of opposing movements. At least one of the reference intended movements may be restricted to movement of the object according to one of the pair of opposing movements.

The object may comprise a prosthetic limb device having one or more actuators that are configured to be controlled based on the plurality of user's signals.

Determining each of the profile-pairs may comprise matching a first profile and a second profile based on a computed correlation between the first profile and the second profile.

The reference set of profiles may comprise a reference matrix configured to provide a mapping between the plurality of user signals and each of the degrees of freedom of the plurality of degrees of freedom.

The reference matrix may be configured to provide a mapping between the plurality of user signals and an activation coefficient matrix comprising a plurality of coefficients. Each of which may correspond to one respective single degree of freedom of the object.

The reference matrix may be configured to provide a mapping between an estimation matrix and the activation coefficient matrix. The estimation matrix may comprise a plurality of coefficients. Each coefficient of the estimation matrix may be based on a sample of a respective one of the plurality of user signals. The reference matrix may be configured to provide the mapping by regression analysis. The reference matrix may be configured to provide the mapping by linear or non-linear regression. The reference matrix may be configured to provide the mapping by kernel-based regression. The reference matrix and the activation coefficient matrix may be configured to provide a non-negative matrix factorisation of the estimation matrix.

Each of the coefficients of the activation coefficient matrix may correspond to a speed and/or a force or a torque of a movement of a respective degree of freedom of the object. Each coefficient of the estimation matrix may comprise a root mean square of the sample of the respective one of the plurality of user signals. In some examples the estimation matrix may be a power estimation matrix, with coefficients that are representative of the power of the plurality of user signals.

The method may further comprise:
receiving the plurality of user signals from one or more sensors associated with the user;
determining the intended movement of the object based on the plurality of user signals and the reference set of profiles; and
providing one or more control signals for controlling movement of the object in accordance with the intended movement.

The method may further comprise: processing obtained signals to obtain the corresponding desired signal features.

The method may further comprise:
performing a constrained optimisation computation to generate an updated reference set of profiles, wherein the constrained optimisation computation is configured to vary coefficients of the reference set of profiles to minimise (or reduce to an acceptably low level) the set difference cost function between: (i) data representative of the plurality of user signals; and (ii) a product of the reference set of profiles with data corresponding to each respective degree of freedom of the object;
receiving an updated plurality of user signals from the one or more sensors associated with the user;
determining an updated intended movement of the object based on the plurality of updated user signals and the updated reference set of profiles; and
providing a one or more updated control signals for controlling movement of the object in accordance with the updated intended movement.

The method may further comprise:
performing a constrained optimisation computation to generate an updated reference matrix, wherein the constrained optimisation computation is configured to vary coefficients of the reference matrix to minimise (or reduce to an acceptably low level) the set difference cost function between (i) the estimation matrix and (ii) a product of the reference matrix with the activation coefficient matrix;
receiving an updated plurality of user signals from the one or more sensors associated with the user;
determining an updated intended movement of the object based on the plurality of updated user signals and the updated reference set of profiles; and
providing one or more updated control signals for controlling movement of the object in accordance with the updated intended movement.

The constrained optimisation computation may be further constrained to require a sparseness of the reference matrix to be within a predetermined range.

There may be provided a computer program product configured to perform any method disclosed herein.

There may be provided an apparatus comprising:
a processor; and
a memory including computer program code;
wherein the memory and the computer program code are configured to, with the processor, cause the apparatus at least to perform any method disclosed herein.

The apparatus may further comprise a memory with prior data which may be used to cause the apparatus at least to perform any method disclosed herein. For example, prior data stored in memory can be used for determining an updated intended movement of the object based on the plurality of updated user signals and the updated reference set of profiles. The prior data may include one or more user signals (which can be myoelectric signals in some examples) and/or estimation matrices along with the corresponding intended movements.

The apparatus may further comprise the object. The object may comprise a prosthetic limb device. The object may comprise one or more of: a robot; a drone; an industrial machine; a clinical system; and a computer generated virtual object for display on a display screen.

One or more embodiments will now be described by way of example only with reference to the accompanying drawings in which:

FIG. 2 shows schematically an example embodiment of a method for enabling movement of an object, which can be performed by the processor of FIG. 1a for example;

Figure 1A:
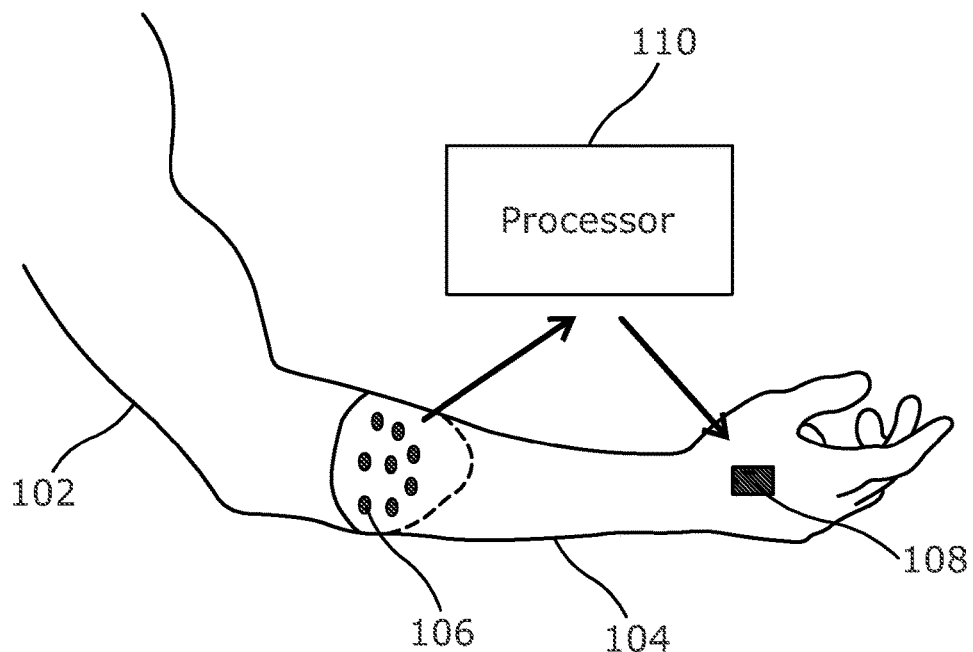
FIG. 1a shows part of a person's arm, which has been amputated below the elbow.

Electromyography (EMG) is the technique that records the electric field potential generated by the depolarization of the muscle fibres' membrane, which affects contraction of the muscle. The recorded signals provide embedded information about the higher levels of the neuromuscular system such as the motor cortex and spinal cord, which in turn relate to movement intention. As will be appreciated from the following discussion, this enables the activity generated by the remaining muscles after amputation, or due to congenital anomalies, to be used to control a prosthesis.

Mechanomyography (MMG) is a technique that records mechanical signals generated in response to the contraction of a muscle. MMG signals may be obtained from accelerometers or microphones placed on the surface of the skin proximal to a particular muscle. MMG signals can also provide information about movement intention.

EMG signals and MMG signals are both examples of myography signals.

Other measurement techniques, in addition to, or instead of EMG or MMG can be used to determine movement intention, for example, gyroscopes or video cameras may be used. It will be appreciated that where a sensor is said to be associated with a user or test subject, the sensor can be associated by virtue of being configured to detect the relevant type of signalling from the user or test subject. Therefore, a video camera can be considered as associated with a user when it is positioned to record images of the user.

In the following disclosure, most discussion will be provided in the context of EMG. However, it will be appreciated that corresponding methods and apparatus can use any myography signals, such as MMG, or other sensor signalling, instead of, or in addition to, EMG.

The physiological concept of "muscle synergies" refers to the coordinated activation of a group of muscles to perform certain tasks. This implies that the central nervous system drives few synergies instead of controlling individual muscles.

Intramuscular electrodes, epimysial electrodes, or surface electrodes on a person's skin can be used for recording EMG signals. However, the thickness of tissue between the targeted muscles and the recording sites—called volume conductor—can vastly influence the EMG signal properties. Such a volume conductor can act as a spatial low pass filter that attenuates the signal amplitude and reduces its bandwidth. Indeed, EMG signal features not only depend on anatomical factors but also physical and acquisition system parameters. These aspects are especially relevant for surface recordings of EMG signals and include: electrode size, inclination and position with respect to the muscle fibre, inter-electrode distance and crosstalk (signal contributions from adjacent muscles).

Features extracted from the EMG signals can be representative of a fibre (intramuscular) or global muscle (surface) activation. This implies a trade-off between the signal quality and the invasiveness of the recording. Intuitively, intramuscular recordings can have higher spatial selectivity and lower volume conductor attenuation than surface EMG.

FIG. 1a shows part of a person's arm 102, which has been amputated below the elbow. A prosthetic arm 104 is shown connected to the remaining portion of the person's arm 102.

The absence of a limb can have terrible consequences for a person in their everyday activities. Arm impairments can be especially severe since they dramatically reduce the capability for a person to interact with the environment, trigger psychological symptoms, and can ultimately yield in disability. Prostheses aim to compensate this lack of functionality. Control mechanisms for prostheses can include passive cosmetic and body-driven technologies. It can be advantageous for myoelectric control of prostheses to be used, that do not require invasive implants and that do not suffer from limited accuracy, which can hinder their development outside a research environment. Therefore, electromyography is considered to be a beneficial method to decode motor commands for prosthetic control.

The design of upper limb prosthetics can depend on the level of amputation, yielding in specific features for trans-radial, trans-humeral and shoulder impairments. The latter cases become especially challenging since more degrees of freedom (DOF) are required to substitute movement of the elbow, while the sources for myoelectric control are more limited. Overall, prosthetic features become more sophisticated the more distal the absence of the limb is. The surgical procedure of target muscle reinnervation appears as a means to extend the capabilities of these prostheses.

Figure 1B:
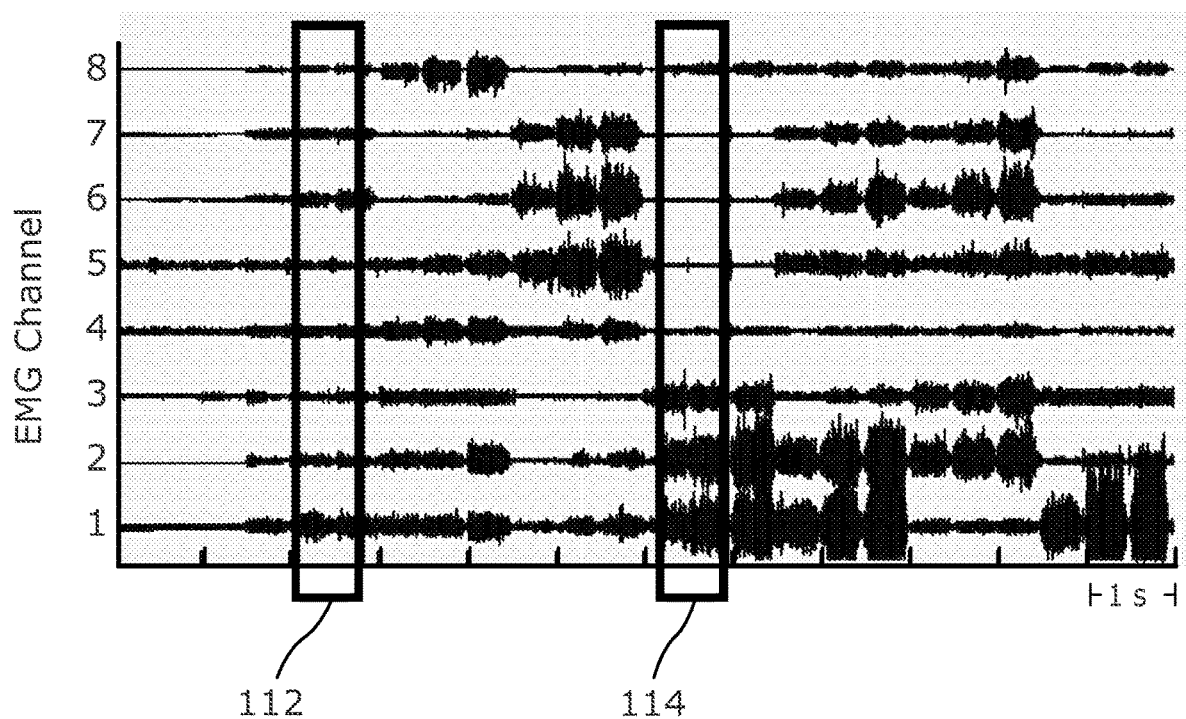
FIG. 1b shows an example of eight EMG signals, which are provided by eight EMG electrodes that can be in contact with a user's skin.

FIG. 1a shows eight EMG electrodes 106 that are connected to the user's arm to record EMG signals. FIG. 1b shows an example of eight EMG signals, which are provided by eight EMG electrodes that can be in contact with the user's skin or implanted under the user's skin. In some examples, the EMG electrodes can be provided in a band around a user's arm, or other limb. The EMG signals are provided to a processor 110 by either a wireless or wired connection. The processor 110 can process the received EMG signals and provide control signals to one or more actuators 108 that are associated with the prosthetic arm 102. For instance, actuators 108 can be provided to move the hand or wrist in this example. Each of these movements can be a degree of freedom (DOF) of the prosthetic limb. In this example, each of the DOFs corresponds to a pair of opposing movements: (i) opening and closing the hand; (ii) rotating the wrist clockwise or anticlockwise; (iii) flexing or straightening the wrist. In examples where the prosthetic limb includes the elbow joint, additional degrees of freedom can be provided, with associated actuators.

In this way, EMG can be used as a source of control for electrically powered hand prostheses, where user motion intention is decoded from the electrical activity of the remnant muscles by processing the EMG signals. In some examples, EMG signals can be recorded from two antagonist muscles, and their contraction intensity can be mapped to the prosthesis movement speed. This can be referred to as proportional control.

Pattern recognition-based control can also be used to enable movement of an object. Pattern recognition-based control is based on an assumption that different motions produce specific contractions patterns visible in EMG features, which are also repeatable with time. Machine learning algorithms can be used to detect these patterns and produce the corresponding predefined movement. Pattern recognition can provide multiple predefined movements with more direct movement transitions. These techniques can yield in high accuracy distinguishing multiple movements. However, pattern recognition-based control disadvantageously cannot readily provide for proportional control of multiple degrees of freedom of an object. Further, pattern recognition-based control requires regular recalibration that is specific to each separate user, unlike embodiments of the present disclosure which can function without necessarily requiring any recalibration.

Pattern recognition-based control can also be used to enable movement of an object. Pattern recognition-based control is based on an assumption that different motions produce specific contractions patterns visible in EMG features, which are also repeatable with time. Machine learning algorithms can be used to detect these patterns and produce the corresponding predefined movement. Pattern recognition can provide multiple predefined movements with more direct movement transitions. These techniques can yield in high accuracy distinguishing multiple movements. However, pattern recognition-based control disadvantageously cannot provide for proportional control of multiple degrees of freedom of an object. Further, pattern recognition-based control requires regular recalibration that is specific to each separate user, unlike embodiments of the present disclosure which can function without necessarily requiring any recalibration.

Some control mechanisms can only enable the activation of a single degree of freedom (DOF) at a time. In which case, the number of DOFs can be extended with a switching function, which preserves a two-channel configuration. This procedure can result in sequential motion control (that is, movements according to multiple DOF individually in sequence), which can be undesirable in some applications, and can also require a cumbersome switching trigger or key such as co-contraction or fast repetition of signal commands.

It has been found that regression systems and physiologically inspired algorithms show potential to address these limitations since they can provide proportional and simultaneous control of multiple DOFs. These approaches can be more intuitive and consistent with the natural activation of the neuromuscular system. Algorithms that can be used include: (i) Linear Regression (LR), which estimates the joint kinematics and kinetics, and (ii) Non-negative Matrix Factorization (NMF), which is based on a muscle synergy model. This model assumes the translation of low dimensional neural commands into higher dimensional muscle activation patterns to affect movements. Further details of these algorithms are provided below.

The success of these algorithms has enabled a change of research focus from the relationship between physical variables and control signals, to an assessment of the ability to perform functional tasks (online performance). For example, it has been found that offline performance, where the users are not able to interact with the control, may not be an accurate predictor of online control performance. The results of a study that evaluated artificial neural networks, LR and NMF, both offline and online processing in goal-directed tasks, showed that although an offline correlation with the kinematics was significantly different between the algorithms, an online performance was extremely similar. This has been interpreted as emphasizing the role of user adaptation via real-time feedback, and the importance of online testing.

Then inventors have found that, surprisingly, subjects can adapt to suboptimal mappings and still achieve good control of the prosthetic limb.

FIG. 2 shows schematically an example embodiment of a method for enabling movement of an object, which can be performed by the processor of FIG. 1a for example. The object has a plurality of degrees of freedom. In this example the object is a prosthetic limb, and the plurality of degrees of freedom include a first pair of opposing movements and a second different pair of opposing movements. In other examples the object can be any physical object, such as a robot; a drone; or industrial machine. Alternatively, the object could be a computer generated virtual object for display on a display screen, which is movable in a virtual space.

FIG. 2 shows method steps 202 to 208, which can be considered as relating to a training/offline method that involves calibration for a plurality of different subjects/people in order to generate reference profiles 210.

FIG. 2 also shows method step 212, which can be considered as processing online/"live" EMG signals in order to generate control signals for moving the prosthetic limb simultaneously with respect to at least two degrees of freedom, using the reference profiles 210. Any reference profile disclosed herein can comprise reference parameters, in some examples. The simultaneous movements can include at least: (i) one of a first pair of opposing movements; and (ii) one of a second different pair of opposing movements.

Advantageously, this method can avoid the need for individual calibration on a per-person basis. This is because it has been found that generating the reference profiles in the manner described below can provide satisfactory performance for different individuals. Also advantageously, the method generates reference profiles that enable simultaneous and proportional control of the prosthetic limb with respect to at least two degrees of freedom using online data.

At step 202, the method includes receiving a first plurality of reference EMG signals 214. (EMG signals may also be referred to as myoelectric signals.) FIG. 2 shows an optional pre-processing step 203 in which raw signal data is pre-processed to provide the first plurality of reference EMG signals 214. Pre-processing can include any type of signal filtering, for example.

The first plurality of reference EMG signals 214 are provided by a respective plurality of different electrodes in contact with a first test subject. The electrodes can be attached to the user's skin or can be implanted. The first plurality of myoelectric signals 214 are generated in response to a plurality of reference intended movements. In some examples, each one of the reference intended movements is restricted to movement of a single degree of freedom of the prosthetic limb, which can be one of a pair of opposing movements. In other examples, the reference intended movements can relate to a combination of two or more degrees of freedom of the prosthetic limb. Either way, the plurality of reference intended movements can, between them, relate to each of the plurality of degrees of freedom of the prosthetic limb. In this example, information about the intended movements is provided as a reference-control signal 216.

The reference-control signal 216 can be automatically generated by a calibration-processor that is used to provide instructions to the first subject to move the prosthetic limb in a particular way. For instance, the calibration-processor may cause an output device (such as a display or a loudspeaker) to provide sequential instructions to the first subject to move the prosthetic limb according to predetermined degrees of freedom; in some applications single degrees of freedom, one at a time. With reference to FIG. 1b, during a first reference period of time 112, the calibration-processor may instruct the first subject to clench their fist. The calibration-processor may then provide a reference-control signal 216 that is indicative of a "first-clenching" degree of freedom movement, and information that allows the method to associate that DOF with the corresponding portions of the EMG signals (that is, those that occur during the first reference period of time 112). Similar processing may be performed for a second reference period of time 114, for example for the subject flexing their wrist.

Returning to FIG. 2, also at step 202 the method involves determining a set of first profiles 218 based on the first plurality of reference EMG signals 214 and the plurality of reference intended movements (in this example as provided by the reference-control signal 216). Each first profile of the first set of profiles 218 corresponds to one or more respective degrees of freedom of the prosthetic limb, and the first set of profiles can relate to each of the plurality of degrees of freedom. For instance, the first set of profiles 218 can be provided as a 2 dimensional matrix whereby: each column in the matrix corresponds to a single DOF; and each row in the matrix corresponds to the value of an EMG signal provided by one of the plurality of electrodes. The first set of profiles (and other profiles described herein) can provide a mapping between received EMG signals and an associated intended movement.

Step 204 is very similar to step 202, and relates to processing a second plurality of reference EMG signals 220, which are provided by a respective plurality of different electrodes in contact with a second test subject. Step 205 is an optional pre-processing step in which raw signals can be pre-processed in a way similar to step 203. At step 204, the method involves determining a set of second profiles 224 based on the second plurality of reference EMG signals 220 and a plurality of reference intended movements 222. Each second profile of the second set 224 also corresponds to one or more respective degrees of freedom of the prosthetic limb, and the second set of profiles 224 can also relate to each of the plurality of degrees of freedom.

At step 206, the method involves determining profile-pairs 226; each profile-pair 226 comprises a first profile and a second profile that correspond to the same degree/degrees of freedom of the prosthetic limb. For example, the method can compare: (i) individual first profiles from the first set of profiles 218, with (ii) individual second profiles from the second set of profiles 220, in order to match individual profiles that relate to the same DOF. These matched profiles can be considered as the profile-pairs 226.

At step 208, the method involves determining the reference set of profiles 210 based on a mathematical combination of the first profile and the second profile of each profile-pair 226. In some examples, the combination can comprise a statistical average of the first profile and the second profile. In this way, the reference set of profiles 210 can, between them, correspond to each of the plurality of degrees of freedom. For instance, in the same way as described above, the reference set of profiles 210 can be provided as a 2 dimensional matrix whereby: each column in the matrix corresponds to a single DOF; and each row in the matrix corresponds to the value of an EMG signal provided by one of the plurality of electrodes. The method can then provide the reference set of profiles 210 for subsequent use as part of the online processing, in order to determine an intended movement of the prosthetic limb based on received user EMG signals 228. Such online processing will be described below with reference to step 212.

At step 212, the method receives a plurality of user EMG signals 228 from a respective plurality of different electrodes in contact with a user, that was not necessarily one of the subjects used for calibration. The electrodes can be attached to the user's skin or can be implanted. Step 212 also determines an intended movement of the prosthetic limb based on the user EMG signals 228 and the reference set of profiles 210. Since the reference set of profiles 210 are not necessarily directly related to the user from which the EMG signals 228 have been provided, advantageously no calibration or training is required by the user in order to successfully control movement of the prosthetic limb. Furthermore, the control signals can operate the prosthetic limb for proportional and simultaneous movements with respect to at least two degrees of freedom of the plurality of degrees of freedom. The intended movement that is determined at step 212 can be represented as one or more control signals 230 for controlling movement of the prosthetic limb in accordance with the intended movement.

Advantageously, "proportional control" of a prosthetic limb, or other object, can be used with one or more of the embodiments described herein. That is, the range of values of a mechanical variable of the prosthesis or other object (such as velocity, force, torque or position) can be mapped in a continuous manner to the corresponding amplitude of the EMG signal. This strategy can provide smooth control. "Direct control" can also be provided, which is an extension of proportional control where different functions are mapped to separate EMG signals.

Advantages associated with the method of FIG. 2 can include:
good robustness, high functionality and safety.
simultaneous and proportional prosthesis control for more natural wrist and hand movements.
the provision of a universal interface. Therefore, it will not need to be customized for a specific user nor prosthesis; instead it will provide control signals that can be associated to multiple degrees of freedom of any upper limb prosthetic device (or other object in different applications) and user in this example. In this way, it will be possible to integrate the interface provided by the method described herein in new prosthetic fittings as well as in prostheses already in use.

Figure 3:
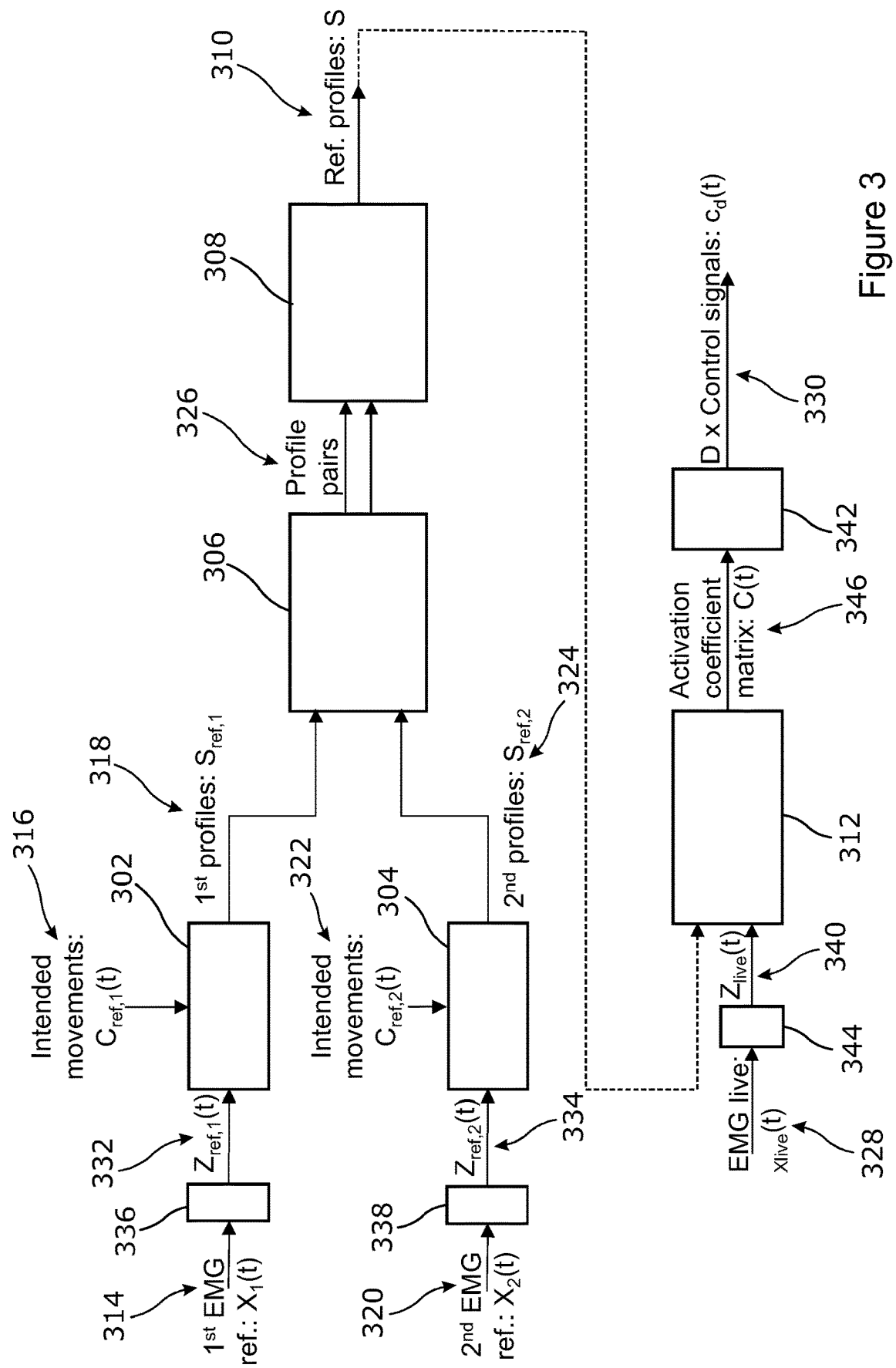
FIG. 3 is similar to FIG. 2, and illustrates a specific example that implements Non-negative Matrix Factorization (NMF) to generate the reference profiles.

FIG. 3 is similar to FIG. 2, and will be used to describe a specific example that implements Non-negative Matrix Factorization (NMF) to generate the reference profiles. NMF can be used to extract muscle synergies in a minimally supervised configuration. As will be described below, in this example only one DOF is activated at a time as part of the calibration trials. It will be appreciated that in other applications, such a restriction of only activating a single DOF at a time may not be required.

In FIG. 3, the method receives $X_1(t)$ 314, which includes N first reference EMG channels from N electrodes attached to a first subject, that were acquired during a calibration operation. In this example, as a pre-processing step 336, the method calculates the root mean squared (RMS) of the N EMG channels $X_1(t)$ 314 to generate a first estimation matrix, $Z_{ref,1}(t)$ 332 (which in this example is a first power estimation matrix). The method also receives a first activation coefficient matrix, $C_{ref,1}(t)$, which is data that corresponds to the intended movements/degrees of freedom of the prosthetic limb that occurred during the calibration operation. Similarly, the method receives N second reference EMG channels, $X_2(t)$ 320 from a second subject, and calculates 338 the root mean squared (RMS) to generate a second estimation matrix, $Z_{ref,2}(t)$ 334 (which in this example is a second power estimation matrix). The method also receives a second activation coefficient matrix, $C_{ref,2}(t)$. As will be described in detail below, the method determines a reference profile matrix S 310, for subsequent use in online processing.

Generally, a power estimation matrix Z(t) can be expressed as the linear mixture:

$$Z(t) = SC(t) \quad (1)$$

Where C(t) is an activation coefficient matrix that corresponds to latent control signals with dimension 2D. D is the number of degrees of freedom of the prosthetic limb.

The reference profile matrix S can also be referred to as a synergy matrix, where $S \in \mathbb{R}^{N \times 2D}$.

During the training processing, at steps 302 and 304 (after the pre-processing at steps 336 and 338) the method processes at least the following input signals:
- a first power estimation matrix $Z_{ref,1}(t)$ 332, which is representative of the first EMG signals $X_1(t)$ 314;
- a first activation coefficient matrix $C_{ref,1}(t)$ 316, which is representative of a plurality of reference intended movements associated with the first EMG signals X1(t) 314;
- a second power estimation matrix $Z_{ref,2}(t)$ 334 which is representative of the second EMG signals $X_2(t)$ 320; and
- a second activation coefficient matrix $C_{ref,2}(t)$ 322, which is representative of a plurality of reference intended movements associated with the second EMG signals $X_2(t)$ 320.

The training processing generates a reference profile matrix S 310 as an output.

During the online processing, the method receives N user EMG channels, $X_{live}(t)$ 328 from N electrodes as an input, and uses the synergy matrix S 310 (determined from the training processing) to generate D control signals $c_d(t)$ 330 for controlling movement of the prosthetic limb.

In this example, each degree of freedom includes a pair of values: a DOF-positive-direction-value and a DOF-negative-direction-value. For example, opening a hand can represent a DOF-positive-direction-value; and closing the hand can represent a DOF-negative-direction-value. That is, a DOF can have a positive direction or a negative direction, which are represented separately in the activation coefficient matrix C(t). This is because NMF imposes the restriction that all terms in the equation are non-negative to approximate a solution. The positive and negative directions can be mutually exclusive, in that it is only possible to move the prosthetic limb in a direction represented by one of the positive and negative directions at any instant in time.

The activation of the d-th DOF can be described by the non-negative coefficients $c_d^p$ and $c_d^n$, corresponding to the positive and negative directions of the d-th DOF respectively. Applying this limitation to equation (1), it can be rewritten as $$Z(t) = \begin{bmatrix} S_1^p & S_1^n & \ldots & S_D^p & S_D^n \end{bmatrix} \begin{bmatrix} c_1^p(t) \\ c_1^n(t) \\ \vdots \\ c_D^p(t) \\ c_D^n(t) \end{bmatrix} \quad (2)$$

Where:
Z(t) is a row of N coefficients, where each coefficient represents the power in a signal received from one of the EMG channels (X(t)); and
each coefficient $S_d^n$ or $S_d^p$ shown in the above synergy matrix represents a vector of N reference values.

In relation to the calibration trials, the indeterminacy of equation (2) can be addressed by activating a single DOF at a time, to find a solution. If only the i-th DOF is active, the activation coefficients $c_d^p$ and $c_d^n$ in $C_{ref}(t)$ 316, 322 become zero for all d≠i, simplifying the previous equation (2) into:

$$Z_i(t) = \begin{bmatrix} S_i^p & S_i^n \end{bmatrix} \begin{bmatrix} c_i^p(t) \\ c_i^n(t) \end{bmatrix} \quad (3)$$

Where $Z_i(t)$ is the power estimation of the N EMG channels when only the i-th DOF is active. This approach enables the calculation of the columns in S in a DOF-wise manner, by solving the set of D equations formulated as (3).

In this way, calibration data can be used to estimate the synergy matrix S, which will be employed in the estimation of the control signals during the online ("live") validation phase.

It will be appreciated that in other examples, equation 2 may be solved by using constrained optimisation techniques that do not require the limitation to activating one DOF at a time. In such examples, a constrained optimisation may also impose conditions on the synergy matrix S by, for example, limiting S to have a sparseness within predetermined range.

More particularly, step 302 can process the first power estimation matrix $Z_{ref,1}(t)$ 332 and the first activation coefficient matrix $C_{ref,1}(t)$ 316, in order to determine a first profile matrix $S_{ref,1}$ 318 in a DOF-wise manner as discussed above. In this way, the method can determine the first profile matrix $S_{ref,1}$ 318 by: (i) determining a first power estimation matrix $Z_{ref,1}(t)$ 332 representative of samples of the first plurality of reference myoelectric signals $X_1(t)$ 314 for the reference intended movements; (ii) determining or receiving a first activation coefficient matrix $C_{ref,1}(t)$ 316, which is representative of a plurality of reference intended movements associated with the first plurality of reference myoelectric signals; and (iii) determining a factorisation of the first power estimation matrix $Z_{ref,1}(t)$ 332 into the first profile matrix $S_{ref,1}$ 318 and the first activation coefficient matrix $C_{ref,1}(t)$ 316.

Each coefficient of the first power estimation matrix $Z_{ref,1}(t)$ 332 can comprise a root mean square of a sample of a respective one of the first reference EMG signals $X_1(t)$ 314. A non-zero coefficient of the first activation coefficient matrix $C_{ref,1}(t)$ 316 can correspond to a speed and/or a force or a torque of a movement of the associated degree of freedom of the prosthetic limb.

Determining the first profile matrix $S_{ref,1}$ 318 at step 302 can comprise performing a constrained optimisation computation configured to reduce a difference between (i) the first power estimation matrix $Z_{ref,1}(t)$ 332, and (ii) a product of the first profile matrix $S_{ref,1}$ 318 and the first activation coefficient matrix. $C_{ref,1}(t)$ 316. The constrained optimisation computation can be constrained to require a sparseness of the first profile matrix $S_{ref,1}$ 318 to be within a predetermined range.

Similarly, step 304 can process the second power estimation matrix $Z_{ref,2}(t)$ 334 and the second activation coefficient matrix $C_{ref,2}(t)$ 322, in order to determine a second profile matrix $S_{ref,2}$ 324.

In this way: the power estimation matrices $(Z_{ref})$ are representative of reference EMG signals X(t); the activation coefficient matrices $C_{ref}(t)$ are representative of reference intended movements; and the profile matrices $S_{ref}$ are examples of sets of profiles.

At step 306, the method generates profile-pairs 326 by matching: (i) a first profile of the first profile matrix $S_{ref,1}$ 318; and (ii) a second profile of the second profile matrix $S_{ref,2}$ 324. This matching can be based on a computed correlation between the first profile matrix $S_{ref,1}$ 318 and the second profile matrix $S_{ref,2}$ 324, in order to match profiles that relate to the same DOFs. It will be appreciated that the profile-pairs 326 can be represented in a number of ways. For instance, the individual profiles in the one of the first and second profile matrices $S_{ref,1}$ 318, $S_{ref,2}$ 324 may simply be reordered such that they align with the individual profiles in the other matrix. This is one example of how to match the channel locations.

The matching at step 306 can be beneficial because NMF is a semi supervised algorithm, which may not result in a consistent order of the profiles in the first and second profile matrices $S_{ref,1}$ 318; $S_{ref,2}$ 324. That is, with NMF, the synergies in a determined synergy matrix S may not always be aligned in the same way.

It will also be appreciated that in some examples there may be more than two sets of calibration data, and that any number of reference EMG signals X(t) can be processed. Therefore, although method step 326 is described here as matching/aligning pairs of profiles, in other examples method step 326 can match/align more than two profiles in order to determine profile-sets that relate to three or more profiles.

At step 308, the method involves determining the reference profile matrix S 310 based on a linear combination of the values of the coefficients in the first profile and the second profile of each profile-pair 326. As indicated above, beneficially, generating the reference profile matrix S 310 in this way enables it to be used by various users without requiring bespoke calibration/training for individual users. Also, the reference profile matrix S 310 is suitable for subsequent use in controlling a prosthetic limb with simultaneous movements with respect to at least two degrees of freedom.

Turning now to the online processing, step 344 performs pre-processing that calculates the root mean squared (RMS) of the received N user EMG channels, $X_{live}(t)$ 328 to generate a live power estimation matrix, $Z_{live}(t)$ 340.

At step 312, the method processes the live power estimation matrix, $Z_{live}(t)$ 340 and the reference profile matrix S 310 in order to determine a live activation coefficient matrix C(t) 346. The Moore Penrose algorithm can be used to compute the pseudoinverse S+ of S to solve:

$$C(t) = S^+ Z(t) \tag{4}$$

C(t) can be normalized with respect to the maximum value to avoid differences in magnitude obscuring some DOF components.

In this example, at step 342, the activation coefficients $c_d^p$ and $c_d^n$ of the live activation coefficient matrix C(t) 346 are combined to generate a control signal $c_d(t)$ 330 for each DOF. For instance, where a degree of freedom includes a pair of values: a DOF-positive-direction-value $c_d^p$ and a DOF-negative-direction-value $c_d^n$; the pair of values can be added together to provide a control signal/value for that DOF.

For an example where there are two DOFs (D=2), the resulting control signals 330 can be:

$$c_1(t) = c_1^p(t) - c_1^n(t) \tag{5}$$

$$c_2(t) = c_2^p(t) - c_2^n(t) \tag{6}$$

More generally, the method provides D control signals, $c_d(t)$ 330, where D is the number of degrees of freedom. Each of the control signals $c_d(t)$ 330 can be provided to one or more actuators associated with the prosthetic limb, or they can be combined by a processor in any appropriate way before being provided to the actuators. Such combination may enable the control signals $c_d(t)$ 330 to be made suitable for the specific actuators that are associated with the prosthetic limb that is being used. In this way, a prosthetic limb, having one or more actuators, can be controlled based on a plurality of user EMG signals $X_{live}(t)$ 328.

Therefore, control signals can be provided that are directly related to the DOFs, allowing linear combinations of primitive signals for simultaneous control.

Advantageously, using the synergy matrices/activation control matrices/obtained by NMF, as described above, can be fairly robust to the number of electrodes and location of the electrodes. This can therefore yield in similar online control performances irrespective of the specific electrode alignment used in the online processing, and also means that individual bespoke calibration is not required for each person that wants to use the online processing.

In other examples, not specifically illustrated, any regression techniques can be applied to estimate the kinetics and kinematics of the movement based on received EMG signals. In this way, appropriate control signals can be directly estimated from the EMG signals in a continuous fashion, providing proportional and simultaneous control of several DOF.

In one example, linear regression (LR) can be used. The aim of LR in this specific application is to find the weights of the linear combination:

$$\hat{Y} = W^T X + \omega_0 \tag{7}$$

Where $\hat{Y}$ is the estimate of $Y \in R^{D \times T}$, the D dimensional control output for every time instant T, $X \in R^{F \times T}$ is the F dimensional feature vector for every T time instant, $W \in R^{F \times D}$ corresponds to the regression coefficients and $\omega_0$ is the bias term to compensate possible offsets. For simplicity, X is extended with a row of T ones to include the bias in W. The feature vector X is usually an estimator of the power of the signal such as the root mean square (RMS).

W is obtained by minimizing the mean squared error of the training trials (equivalent to the user EMG signals described above) with respect to the provided labels (equivalent to the reference intended movements described above). The least mean square solution in closed form is given by:

$$W = (XW^T)^{-1} XY \tag{8}$$

In some examples, the processing described herein can be extended such that the interface is adaptive and so can be adjusted to individual users and user needs, or perturbations of either the input signals or the environment in which it is being used. This adaptation should be carried out in a minimally supervised way and by updating the reference set of profiles. This approach may be used for any regressor-based algorithm.

For example, the method may comprise performing a constrained optimisation computation to generate an updated reference set of profiles/reference profile matrix S 310. The constrained optimisation computation may vary coefficients of the reference set of profiles/reference profile matrix S 310 to minimise (or reduce to an acceptably low level) the set difference cost function between:
  (i) data representative of the plurality of user myoelectric signals (which can be the live power estimation matrix $Z_{live}(t)$ 340 in FIG. 3); and
  (ii) a product of (a) the reference set of profiles/reference profile matrix S 310, and (b) data corresponding to each respective single degree of freedom of the object (which can be the activation coefficient matrix C(t) 346 in FIG. 3).

Such a constrained optimisation computation can be constrained to require a sparseness of the reference matrix to be within a predetermined range or a certain data transformation such as kernel mappings, in some examples.

The method can receive an updated plurality of user EMG signals ($X_{live}(t)$ 328) from the respective plurality of different electrodes in contact with the user; and determine an updated intended movement of the object (and in turn an updated activation coefficient matrix C(t) 346 in FIG. 3) based on the plurality of updated user EMG signals ($X_{live}(t)$ 328) and the updated reference set of profiles. The method can then provide one or more updated control signals ($c_d(t)$ in FIG. 3) for controlling movement of the prosthetic limb in accordance with the updated intended movement.

Such examples can use machine learning algorithms that will allow for increased user accuracy and performance over time without the need of retraining the hand each time it is attached to the user. These algorithms can be implemented in a hardware chip secured to the wrist that can communicate wirelessly with the prosthesis, in some examples.

As indicated above, the examples described herein can find application beyond the areas of prosthetic control. The described interface can be provided by a general controller that can have applications in the gaming, gadget and IT industry, teleoperation, health and sports technologies, safety and security research and application areas, as non-limiting examples.

It will be appreciated that two degree of freedom approach described above can readily be extended to more control signals, based on the teachings within this document. For instance, the conceptual framework described herein can be used with a large number of sensors with high signal quality, and with appropriate processing and signal conditioning both at the input and output level.

Furthermore, the neuromuscular interface described in this document can be either a part, or a central concept of a higher-level control approach by complementing other interfaces through sensory fusion. This can be achieved by extending the current inputs of the interface so that they can handle signals received from other modalities (e.g. force, IMUs, motion capture, etc.) and in such way as to deliver control that can be mapped as needed in any of the areas of application identified herein. For instance, examples described herein can process EMG signals in combination with mechanomyogram (MMG) signals and/or other sensor information such as mechanomyography, gyroscopes, accelerometers, etc. Also, outputs of the proposed system can in the same or similar way be fused with other modalities in order to generate the desired control signals.

It will also be appreciated that any suitable apparatus or computer program can be configured to perform any method disclosed herein. Such an apparatus may include a processor, and can also include a memory including computer program code. The memory and the computer program code can, with the processor, cause the apparatus to perform any method described herein.

Study—Experimental Method and Results

The aim of this study is to assess user adaptation from: 1) different online sessions and 2) when no subject-specific calibration has been performed. LR and NMF were used to assess the most robust approach to overcome the expected variability. The online control performance using optimal and suboptimal LR and NMF mappings were compared in a virtual reality task. It was found that the NMF synergies were more consistent in time and across subjects than LR, since the estimated synergies are an optimization mechanism of the central nervous system to control coordinate group of muscle contractions.

1. Experimental Methods

This experiment compared the online control performance using optimal and suboptimal LR and NMF mappings in a virtual reality task. The experiment was divided into two sessions: 1) baseline (optimal vs. suboptimal subject-specific mappings) and 2) non-subject-specific mappings, with respect to an updated calibration from the subject (optimal subject-specific calibration). Sessions were on average two days apart.

1.1 Subjects

Ten able-bodied subjects (23-30 years old, 4 females and 6 males, all right hand dominant) participated in this protocol. All experiments were in accordance with the declaration of Helsinki and were approved by the local ethics committee.

1.2 Experiment Setup

During the experiment, subjects sat in a chair in front of a computer screen. Surface EMG signals were recorded using eight bipolar stainless steel dry electrodes (Myo Armband, Thalmic Labs), which were equally distributed around the maximum diameter of the right forearm. The position of the electrodes was outlined with a surgical marker for consistency across sessions. Subjects were asked to keep their right arm relaxed, extended in the sagittal plane at the side of the body, with the hand in a neutral position (fingers pointing down and thumb facing the front).

1.3 Signal Processing

Signal processing and virtual reality display were carried out in Matlab 2016a running on a i7-7700HQ at 2.80 GHz laptop with 16 GB of RAM. Data was processed in blocks of 40 ms corresponding to the update rate of the entire system. Signals were sampled at 200 Hz (8-bit accuracy) and digitally filtered by a fifth order Butterworth high pass filter (5 Hz cut off frequency) and a fifth order Butterworth low pass filter (90 Hz cut off frequency). Powerline interferences at 50 Hz were cancelled by a second order band stop Butterworth filter.

Data was queued in a 4 s buffer after pre-processing, to extract the features and display the feedback (updated every 40 ms).

The root mean square (RMS) of each EMG channel was computed from the data buffer in windows of 160 ms, complying with the acceptable controller delay for the average prosthetic user. The windows had 120 ms overlap due to the update rate of the controller. RMS was used as a feature for both algorithms.

1.4 Calibration Protocol

In the virtual reality environment, an onscreen cursor was presented to the subjects to guide them during movement execution. Movements were mapped into a two-dimensional coordinate system of 400×180 device-independent pixels (dp), centered at the origin. The horizontal axis was mapped to extension/flexion, the vertical to radial/ulnar deviation, and the origin to rest. The cursor moved at a constant speed from the origin to the 80 dp of the corresponding movement in 1.2 s, dwelled for 0.5 s and returned to rest in 1.2 s, where it stopped for 2.5 s. Between repetitions, subjects were allowed to rest for at least 3 s to avoid fatigue. Each DOF was repeated 4 times.

1.5 Mapping Algorithms

The RMS of the calibration data was fed to LR and NMF to create a continuous control mapping of the virtual space to calculate the weighting matrix and synergies. The obtained regression and synergy mappings were applied during the online validation phase to estimate the cursor's position (D=2 corresponding to the number of DOF).

1.6 Postprocessing

Mapping directly the control estimate into a cursor position would result in a relatively unsteady control caused by the stochastic nature of EMG. Thus, a simple moving average filter was applied to compensate this effect. Its length was adjusted for each run between 5-7 samples to provide a smooth control.

In addition, each direction of the output estimate was multiplied by a scaling factor, which was finely tuned to ensure that subjects could reach the entire area of the target display.

1.7 Validation Protocol

Figure 4:
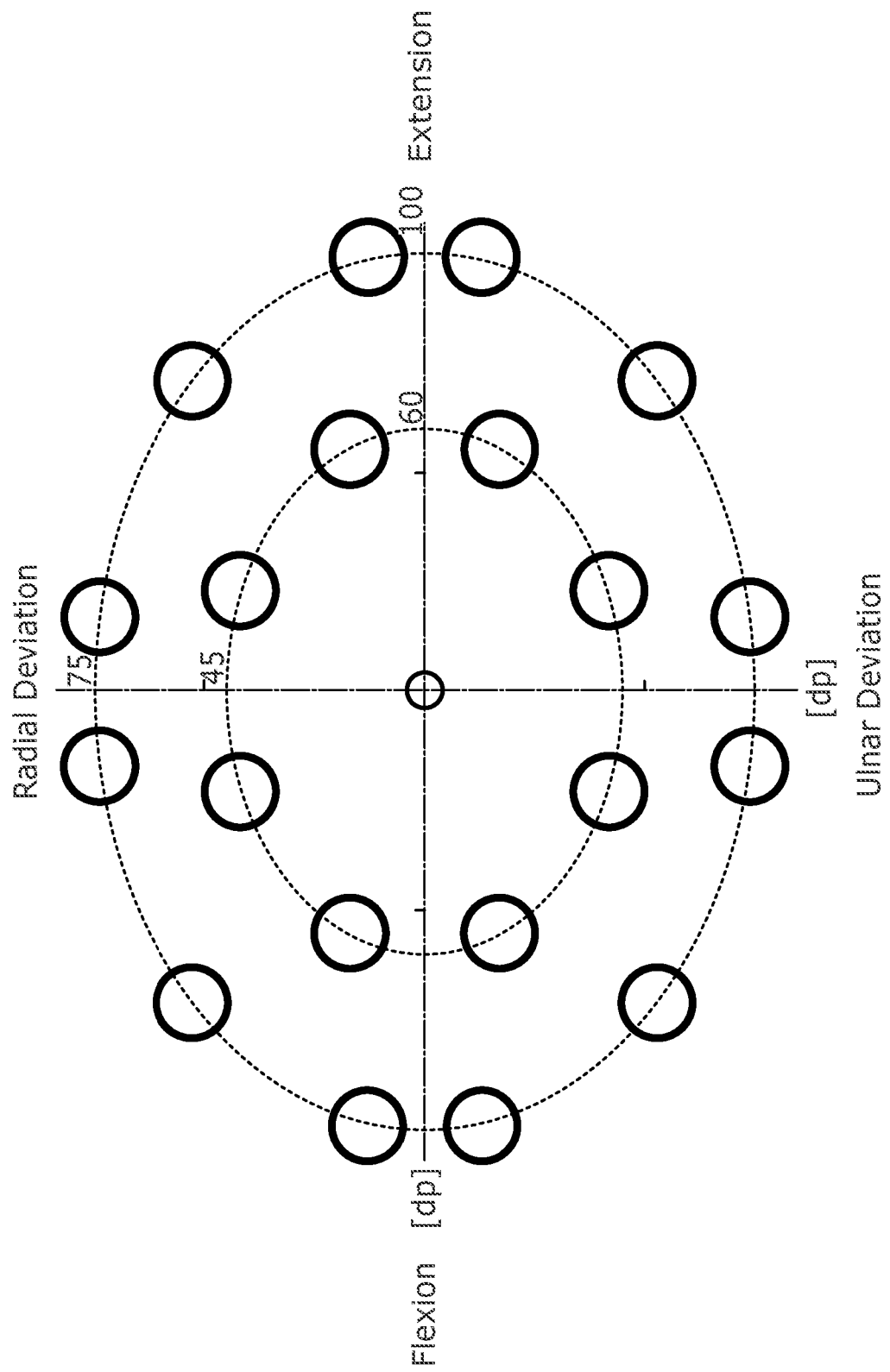
FIG. 4 shows, for an experimental method, a target distribution in the subjects' virtual reality window.

FIG. 4 shows the target distribution in the subjects' virtual reality window. The dotted lines represent the target elliptical trajectories. Dark circles correspond to the targets. The small circle in the origin is the cursor. The horizontal axis was mapped to Extension (positive direction) and Flexion (negative direction). Similarly, the vertical axis was mapped to Radial deviation (positive) and Ulnar deviation (negative) and with less baseline oscillations than LR.

The generated mappings were used for the real-time control of an onscreen cursor in a two-dimensional coordinate system in a goal-oriented manner. During each testing phase, twenty circular targets of 8 device-independent pixels (dp) appeared on screen. The targets followed two elliptic trajectories (as shown in FIG. 4) with major and minor axes corresponding to (100 dp, 75 dp) and (60 dp, 45 dp), respectively. Targets in the outer ellipse were placed at angles of 7, 37 and 77 degrees; mapped to the other quadrants by adding 90, 180 and 270 degrees, respectively (as shown in FIG. 4). The inner ellipse targets were set at angles of 17 and 61 degrees, mapped to the remaining quadrants as mentioned before. The targets' order of appearance was randomized for each experiment. In each trial two targets were shown: the current one in a thick solid line and the following one in a thin dotted line for preparation. To complete the task successfully, target had to be reached in less than 20 s and dwelled inside it for 300 ms.

Subjects were asked to rest between tasks, so the cursor was always at the origin at the beginning of the trials.

1.8 Experiment Protocol

The goal of the experiment was to evaluate the real-time myoelectric control of the onscreen cursor using different regression and synergy mappings. It was divided in two sessions separated by two days.

In the first session, subjects calibrated the system and tested the corresponding LR and NMF mappings (Optimal Subject-Specific of the day 1, OSS1). The testing order was randomized and balanced among subjects.

The second session involved six tests carried out in a randomized and balanced order among subjects. For each algorithm, three mappings were used: subject's own one from the previous session (Suboptimal Subject-Specific, SSS), subjects' own mapping after calibrating in session two (Optimal Subject-Specific of the day 2, OSS2), and the mean of the of the other participants' mappings from session one, without including the evaluated subject, (Non-Subject-Specific, NSS).

The aim of the experiment was to compare the differences in performance when subjects used their optimal mappings after a calibration session, and the performance achieved using suboptimal and subject-independent mappings.

1.9 Metrics and Statistical Analyses

The Normalized Dot Product (NDP) was used to compare the estimated synergy matrixes and regression weights. Greater values of NDP indicate higher similarity between the compared weights. The NDP was computed between subjects' mappings within OSS1 and OSS2, and within subjects' mappings between OSS1-OSS2, OSS1-NSS and OSS2-NSS. The aim of this analysis was to assess the differences between subjects' optimal mappings and the within-subject variability between the sessions.

To quantify the performance of the real-time control system, six predefined metrics were calculated:

1. Completion rate: number of successful targets divided by the total
2. Completion time: average time needed to successfully reach a target
3. Throughput: mean of the ratio between the index of difficulty $$ID = \log_2\left(1 + \frac{\text{target}_{distance}}{\text{target}_{width}}\right)$$

and the completion time

4. Path efficiency: straight-line distance to the target divided by the travelled path
5. Average speed: Average non-zero speed of the cursor
6. Overshoot: Number of times the cursor entered the target non-successfully divided by the total number of targets The absence of outliers was checked by examining the studentized residuals for values greater than ±3. Normal distribution of the metrics was assessed by Shapiro Wilk's test of normality on the studentized residuals. The only non-normally distributed metric was completion rate. Therefore, two Friedman tests with pairwise comparison and Bonferroni correction were carried out for each algorithm to evaluate differences between mappings in CR.

To determine the differences in performance between the mappings for the normally distributed metrics, two-way repeated measures analysis of variance (ANOVA) was used with 'Algorithm' (LR and NMF) and 'Mapping' (OSS1, OSS2, SSS and NSS) as fixed factors for all the metrics. The reduced ANOVA with only main factors (one-way repeated measures) was run if no two-way interaction was detected. If main effects in the mapping factor were detected, the Bonferroni pairwise comparison was used to identify the significant levels. Results were considered significant if $p \leq 0.05$. Mauchly's test of sphericity was used to check if the variance of the differences between levels was equal.

2. Results

Figure 5:
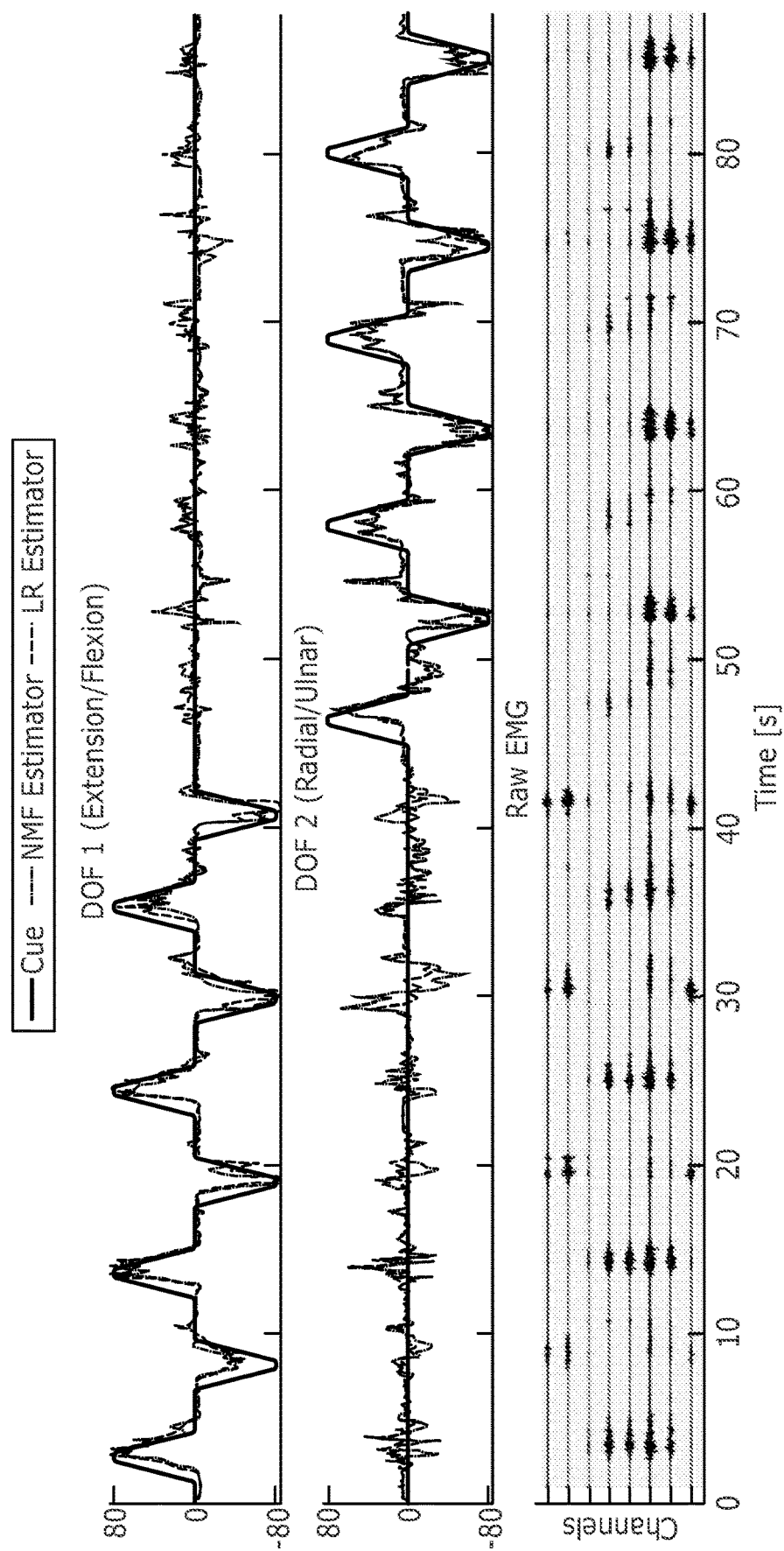
FIG. 5 shows experimental results, which are representative EMG and estimated control signals from one subject during calibration.

FIG. 5 shows representative EMG and estimated control signals from one subject during calibration. A representative example of surface EMG recorded during calibration is shown in the lower plot. In the upper plots, the thick solid lines in dark blue correspond to the cues presented to the subjects in dp. The solid light blue and dashed green lines are the estimated output of the OSS NMF and LR estimators, respectively. The cues provided to the subject in the VR environment are depicted per DOF by solid black lines.

2.1 Weight Analysis

Figure 6:
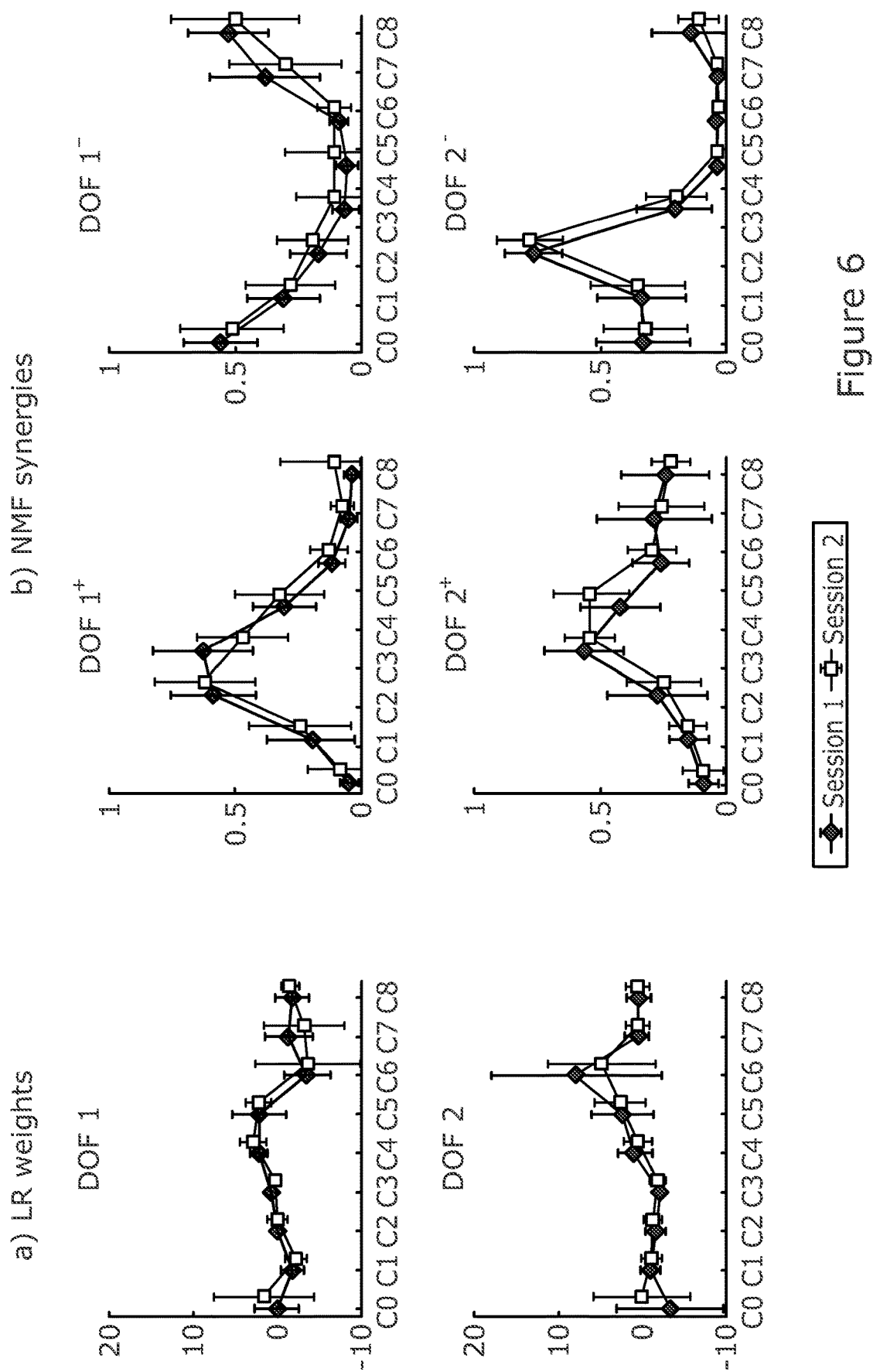
FIG. 6 shows experimental results, which are the profiles of the averaged regression weights and NMF synergies across subjects for each DOF and session.

FIG. 6 shows the profiles of the averaged regression weights and NMF synergies across subjects for each DOF and session (black—session one; grey—session two). Note the change in scale between regression weights and NMF synergies.

Figure 7:
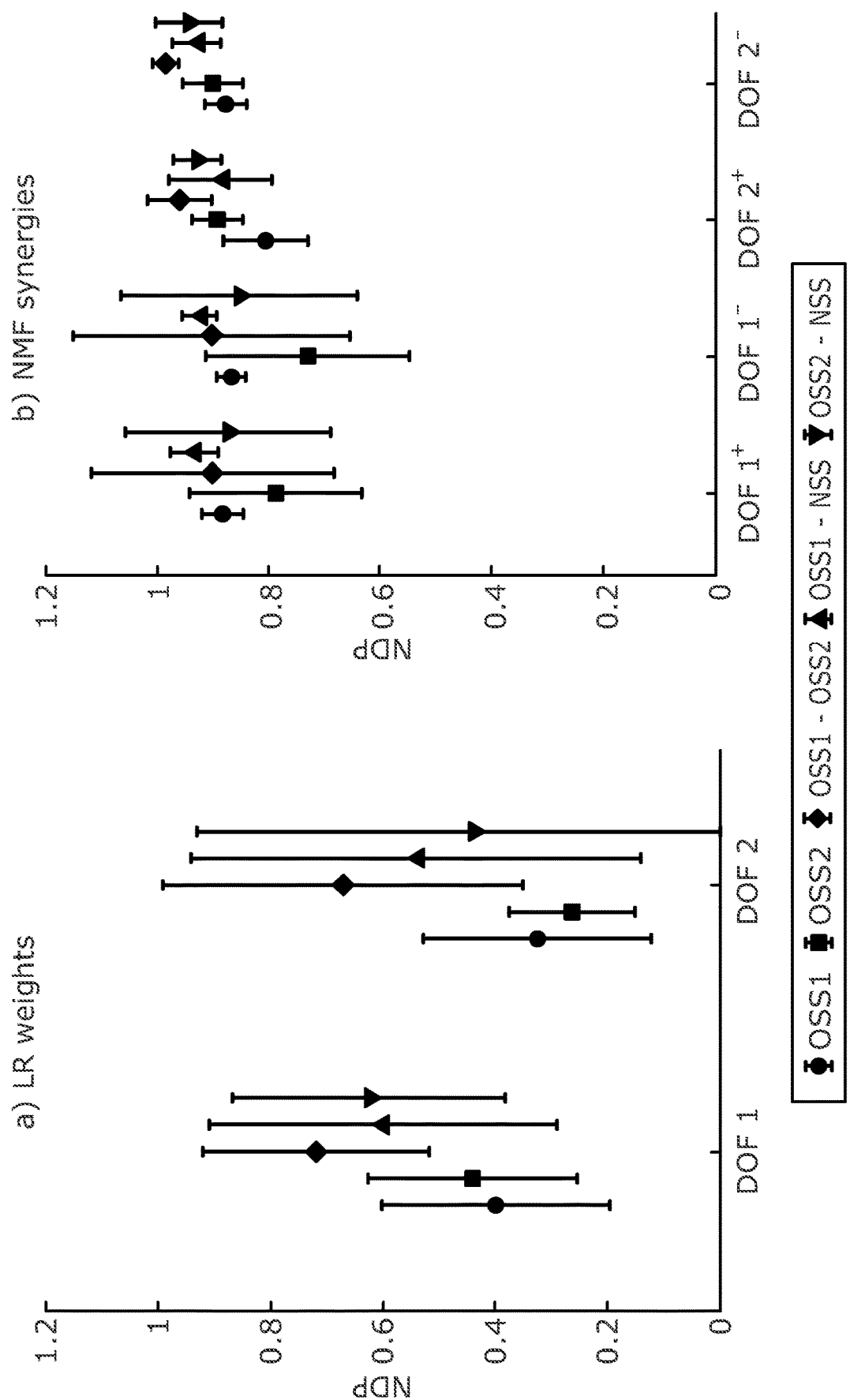
FIG. 7 shows experimental results, which are the mean and standard deviation of Normalized Dot Product (NDP) between the estimated a) linear regression weights and b) synergies.

FIG. 7 shows the mean and standard deviation of Normalized Dot Product (NDP) between the estimated a) linear regression weights and b) synergies. Circles and squares represent the between-subject NDP within the OSS calibrations of session 1 and session 2, respectively. Diamonds correspond to the within-subject NDP between sessions. Finally, the up and down triangles show the within-subject NDP between the NSS and OSS mappings from session 1 and 2 respectively. Synergies present lower between-subject variability than linear regression weights. Within-subject variability between the sessions is quite large in LR, whereas in NMF depends on the DOF.

As expected, higher overall NDP was observed in NMF than in LR (as shown in FIG. 7). Indeed, the analysis between subjects (OSS1 and OSS2 in FIG. 5.3) showed higher similarity in NMF than in LR. The comparison within subjects, between sessions (OSS1-OSS2) increased the NDP for both algorithms, although in LR (DOF 1:0.72±0.20, DOF 2: 0.67±0.32) was relatively low compared to NMF (0.90±0.22, 0.90±0.25, 0.96±0.06, 0.98±0.02 for DOF 1+, DOF 1−, DOF 2+ and DOF 2− respectively). Similarly, the NDP was higher between OSS-NSS than between subjects (OSS), for both algorithms. For NMF, the degree of similarity was quite close to the difference between sessions within subjects.

2.2 Online Cursor Control Performance

Figure 8:
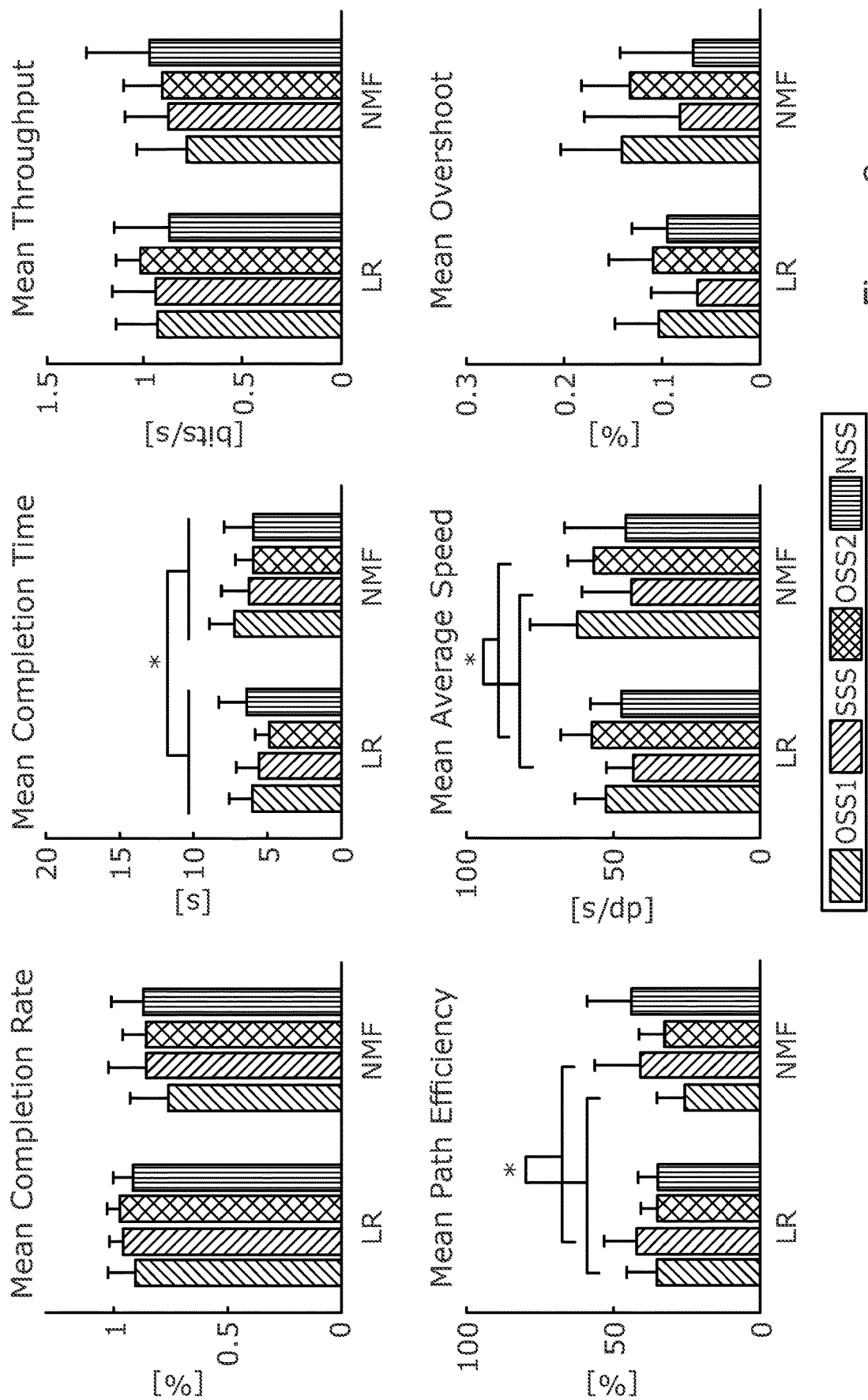
FIG. 8 shows a summary of the cursor control online performance of the experimental results.

FIG. 8 shows a summary of the cursor control online performance, with the grand mean of CR, CT, TP, PE, AS and OS per algorithm and session configuration.

More particularly, FIG. 8 shows a summary of the online performance in terms of completion rate (CR), completion time (CT), throughput, path efficiency (PE), average speed (AS) and overshoot for LR and NMF mappings from the two sessions of cursor control (in different colour). The results are averaged across subjects and the error bars indicate the standard deviation. Note the different scales and units of the axes. Asterisks mark statistical significances. The two-way repeated measures ANOVA showed no significant two-way interaction between the mapping and the algorithm for all metrics. Significant differences CT were found between algorithms ($p=0.038$). PE was significantly higher in SSS than in OSS1 ($p=0.026$), whereas AS was significantly higher in OSS2 than in SSS ($p=0.025$).

During the task, most of the targets were successfully hit for both algorithms as shown by CR values (LR: 91.00±11.50%, 95.00±6.43%, 98.00±4.83%, 91.50±8.51%; and NMF: 75.50±17.87%, 86.00±16.80%, 86.00±10.22% and 86.50±14.54%, for OSS1, SSS, OSS2 and NSS respectively). Although CR was statistically significantly different between sessions for LR ($\chi^2(3)=8.230$, $p=0.041$), the pairwise comparison with Bonferroni correction did not show any significance ($p>0.05$). On the other hand, no statistically significantly difference was found between the sessions in CR for NMF ($\chi^2(3)=4.031$, $p=0.258$).

CT was normally distributed ($p>0.05$), as assessed by Shapiro-Wilk's test of normality on the studentized residuals. In general, CT was shorter in LR than NMF (LR: 6.09±1.51 s, 5.64±1.38 s, 4, 96±0.74 s, 6.37±1.92 s and NMF: 7.20±1.68 s, 6.20±1.91 s, 6.01±1.13 s, 5.95±1.98 s, for OSS1, SSS, OSS2 and NSS respectively). No statistically significant two-way interaction was found between the algorithm and mapping factors ($F(3, 27)=1.100$, $p=0.366$). Subsequently, the reduced ANOVA, indicated significant difference in CT for the algorithm ($F(1, 9)=5.892$, $p=0.038$), but not in the mapping ($F(3, 27)=1.430$, $p=0.256$).

TP was normally distributed ($p>0.05$). The two-way interaction between the mapping and the algorithm factors was not statistically significant ($F(3, 27)=1.611$, $p=0.210$). Although LR showed a slight increasing TP trend, in contrast to NMF minor decrease, the pooled algorithm main effect was not significant ($F(1, 9)=2.533$, $p=0.146$). Similarly, no significant mapping main effect was found ($F(3, 27)=0.369$, $p=0.776$).

Overall, low PE percentages were observed for both algorithms (LR: 35.21±10.1%, 41.79±11.05%, 34.96±5.57%, 34.91±6.44%, and for NMF: 26.16±9.05%, 41, 10±15.38%, 32.49±8.64%, 43.67±15.25%, for OSS1, SSS, OSS2 and NSS respectively), which were normally distributed except for LR SSS ($p<0.001$). No significant interaction was found between the algorithm and mapping factors ($F(3, 27)=2.894$, $p=0.054$). The reduced algorithm main effect was not significant ($F(1, 9)=0.102$, $p=0.757$). However, significant difference in PE was found between mappings ($F(3, 27)=4.536$, $p=0.011$). Bonferroni pairwise comparison showed significant difference between OSS1 and SSS ($p=0.026$).

The AS was higher in the OSS than in the SSS and NSS sessions for both algorithms. Values were normally distributed except for NMF SSS ($p=0.037$). No significant interaction was found between algorithm and mapping factors ($F(3, 27)=1.523$, $p=0.231$), nor algorithm main effects ($F(1, 9)=0.838$, $p=0.384$). Statistically significant difference in AS was observed between mappings ($F(3, 27)=4.345$, $p=0.013$). Bonferroni pairwise comparison determined that the only significant difference was between SSS and OSS2 ($p=0.025$).

OS was normally distributed except for NMF SSS ($p<0.001$), NMF NSS ($p=0.006$). No significant two-way interaction was found between the algorithm and mapping factors ($F(3, 27)=1.302$, $p=0.294$). Similar to AS, the OS was lower for SSS and NSS for both algorithms. Indeed, no statistical difference was found in OS between the algorithms ($F(1, 9)=2.321$, $p=0.162$) Although a significant main effect was detected between mappings ($F(3, 27)=3.484$, $p=029$), Bonferroni pairwise comparison rejected it ($p>0.05$).

3. Discussion

The presented study has indicated users' ability to adapt to suboptimal mappings in a goal-oriented virtual task. LR and NMF algorithms were used to provide simultaneous and proportional control of an online cursor. Subjects performed the task during two separated sessions, using optimal subject-specific, suboptimal subject-specific and non-subject specific mappings. Overall online performance was found to be similar regardless of the differences in the provided weights. The obtained results indicated the important roles of feedback and user adaptation in delivering robust myoelectric control and suggest that system training could be minimized for proportional and simultaneous control systems.

3.1 Weight Analysis

As indicated above, the analysis of the employed mappings showed higher between subject and between session consistency for synergies than for regression weights.

In general, synergies showed greater resemblance between subjects (higher between subject NDP in OSS1 and OSS2) than regression weights. This is in agreement with the higher similarity observed between the OSS and NSS mappings, for synergies than for regression weights. This is reasonable if synergies are considered coordinated activations of muscles groups to compensate the actuation of the redundant number of muscles. However, this result might be influenced by NMF's positive restriction which reduces the total possible variability of the mapping.

Regarding differences between sessions within subjects, LR weights showed overall moderate NDP, whereas synergies achieved almost perfect NDP.

3.2 Online Cursor Control Performance

Although the analysis of the weights showed different degrees of similarity between the SSS and NSS calibrations with respect to the OSS mappings (also influenced by the algorithm), their online performance was not significantly different across CR, CT, TP and OS. Contrary to the expectation that higher congruence with the optimal calibration, would yield better results, the absence of two-way interaction between the mapping and algorithm factors indicates that the effect of mapping on the performance does not depend on the algorithm. The significantly faster CT in LR compared to NMF, support user adaptation since LR weights had higher variability than synergies. Hence, these results demonstrate the different levels of users' adaptation and their importance for robust control.

The fact that only significant mapping main effects were found between OSS and SSS for PE and AS, demonstrate that using the generated NSS mapping results in an online performance alike to the optimal one. This yields to the conclusion that performance is independent on the calibration provided.

The invention claimed is:

1. A method for enabling movement of an object, having a plurality of degrees of freedom, by a user, the method comprising:
receiving a first plurality of reference signals from one or more sensors associated with a first test subject, the first plurality of reference signals generated in response to a plurality of reference intended movements;
determining a set of first profiles based on the first plurality of reference signals and the plurality of reference intended movements;
receiving a second plurality of reference signals from one or more sensors associated with a second test subject, the second plurality of reference signals generated in response to a plurality of reference intended movements;
determining a set of second profiles based on the second plurality of reference signals and the plurality of reference intended movements;
determining profile-pairs, wherein each profile-pair comprises a first profile and a second profile that correspond to the same degree of freedom of the object;
determining a reference set of profiles based on a mathematical combination of the first profile and the second profile of each profile-pair; and
providing the reference set of profiles for determining an intended movement of the object based on a plurality of user signals received from one or more sensors associated with the user,
wherein the intended movement comprises simultaneous movements with respect to at least two degrees of freedom of the plurality of degrees of freedom; and
the object comprises a prosthetic limb device having one or more actuators that are configured to be controlled based on the plurality of user signals.

2. The method of claim 1 wherein the plurality of degrees of freedom include a first pair of opposing movements and a second different pair of opposing movements, and the intended movement comprises simultaneous movements of at least:
one of the first pair of opposing movements; and
one of the second different pair of opposing movements.

3. The method of claim 1, wherein:
the first plurality of reference signals comprises a first plurality of reference myography signals;
the second plurality of reference signals comprises a second plurality of reference myography signals; and
providing the reference set of profiles for determining an intended movement of the object based on a plurality of user myography signals.

4. The method of claim 1, wherein determining each of the profile-pairs comprises matching a first profile and a second profile based on a computed correlation between the first profile and the second profile.

5. The method of claim 1, wherein the reference set of profiles comprises a reference matrix configured to provide a mapping between the plurality of user signals and each of the degrees of freedom of the plurality of degrees of freedom.

6. The method of claim 5, wherein the reference matrix is configured to provide a mapping between the plurality of user signals and an activation coefficient matrix comprising a plurality of coefficients, each of which corresponding to one respective single degree of freedom of the object.

7. The method of claim 6, wherein the reference matrix is configured to provide a mapping between the estimation matrix and the activation coefficient matrix, the estimation matrix comprising a plurality of coefficients, wherein each coefficient of the estimation matrix is based on a sample of a respective one of the plurality of user signals.

8. The method of claim 7, wherein the reference matrix and the activation coefficient matrix are configured to provide a non-negative matrix factorisation of the estimation matrix.

9. The method of claim 6, wherein each of the coefficients of the activation coefficient matrix correspond to a speed and/or a force or a torque of a movement of a respective degree of freedom of the object.

10. The method of claim 1, further comprising:
receiving the plurality of user signals from the one or more sensors associated with the user;

determining the intended movement of the object based on the plurality of user signals and the reference set of profiles; and providing one or more control signals for controlling movement of the object in accordance with the intended movement.

11. The method of claim 10, further comprising:

performing a constrained optimisation computation to generate an updated reference set of profiles, wherein the constrained optimisation computation is configured to vary coefficients of the reference set of profiles to minimise the set difference cost function between: (i) data representative of the plurality of user signals; and (ii) a product of the reference set of profiles with data corresponding to each respective degree of freedom of the object;

receiving an updated plurality of user signals from the one or more sensors associated with the user;

determining an updated intended movement of the object based on the plurality of updated user signals and the updated reference set of profiles; and providing a one or more updated control signals for controlling movement of the object in accordance with the updated intended movement.

12. A tangible computer readable medium or a non-transitory computer readable medium configured to perform the method of claim 1.

13. An apparatus comprising:

an object comprising a prosthetic limb device having one or more actuators; and a processor; and a memory at least including a computer program code;

wherein the memory and the computer program code are configured to, with the processor, cause the apparatus at least to perform the method of claim 1.

14. A method for enabling movement of an object, having a plurality of degrees of freedom, by a user, the method comprising:

receiving a first plurality of reference signals from one or more sensors associated with a first test subject, the first plurality of reference signals generated in response to a plurality of reference intended movements;

determining a set of first profiles based on the first plurality of reference signals and the plurality of reference intended movements;

receiving a second plurality of reference signals from one or more sensors associated with a second test subject, the second plurality of reference signals generated in response to a plurality of reference intended movements;

determining a set of second profiles based on the second plurality of reference signals and the plurality of reference intended movements;

determining profile-pairs, wherein each profile-pair comprises a first profile and a second profile that correspond to the same degree of freedom of the object;

determining a reference set of profiles based on a mathematical combination of the first profile and the second profile of each profile-pair; and providing the reference set of profiles for determining an intended movement of the object based on a plurality of user signals received from one or more sensors associated with the user, wherein the intended movement comprises simultaneous movements with respect to at least two degrees of freedom of the plurality of degrees of freedom, the method further comprising:

receiving the plurality of user signals from the one or more sensors associated with the user;

determining the intended movement of the object based on the plurality of user signals and the reference set of profiles; and providing one or more control signals for controlling movement of the object in accordance with the intended movement.

15. The method of claim 14, further comprising:

performing a constrained optimisation computation to generate an updated reference set of profiles, wherein the constrained optimisation computation is configured to vary coefficients of the reference set of profiles to minimise the set difference cost function between: (i) data representative of the plurality of user signals; and (ii) a product of the reference set of profiles with data corresponding to each respective degree of freedom of the object;

receiving an updated plurality of user signals from the one or more sensors associated with the user;

determining an updated intended movement of the object based on the plurality of updated user signals and the updated reference set of profiles; and providing a one or more updated control signals for controlling movement of the object in accordance with the updated intended movement.

* * * * *